United States Patent
Kilpeläinen

(10) Patent No.: US 9,233,201 B2
(45) Date of Patent: Jan. 12, 2016

(54) DEVICE FOR COLLECTION OF FLUID

(75) Inventor: Pekka Kilpeläinen, Saarenkylä (FI)

(73) Assignee: Muovisola Oy, Polvijarvi (FI)

( * ) Notice: Subject to any disclaimer, the term of this patent is extended or adjusted under 35 U.S.C. 154(b) by 1258 days.

(21) Appl. No.: 12/154,219

(22) Filed: May 20, 2008

(65) Prior Publication Data

US 2008/0228156 A1    Sep. 18, 2008

Related U.S. Application Data

(63) Continuation of application No. PCT/FI2006/000335, filed on Oct. 18, 2006.

(30) Foreign Application Priority Data

Nov. 21, 2005    (FI) .................................. 20051185

(51) Int. Cl.
| | |
|---|---|
| A61M 25/00 | (2006.01) |
| A61M 3/02 | (2006.01) |
| A61M 3/00 | (2006.01) |
| A61F 5/44 | (2006.01) |
| A61B 19/00 | (2006.01) |
| A61B 13/00 | (2006.01) |
| A61H 35/00 | (2006.01) |

(52) U.S. Cl.
CPC .............. A61M 3/0287 (2013.01); *A61H 35/00* (2013.01); *A61M 2210/0618* (2013.01); *A61M 2210/0662* (2013.01)

(58) Field of Classification Search
CPC ........... A61M 25/00; A61M 3/00; A61F 5/44; A61B 19/00; A41B 13/00
USPC .................. 604/346, 355–357; 128/849, 853; 2/49.1, 49.2
See application file for complete search history.

(56) References Cited

U.S. PATENT DOCUMENTS

| | | | | |
|---|---|---|---|---|
| 1,597,556 A | * | 8/1926 | Townsend | ...................... 604/357 |
| 2,364,568 A | * | 12/1944 | Tiscornia | ............................ 2/50 |
| 2,423,489 A | * | 7/1947 | Dunn | ............................... 2/49.3 |

(Continued)

FOREIGN PATENT DOCUMENTS

| | | |
|---|---|---|
| DE | 840 750 | 6/1952 |
| DE | 840750 | 6/1952 |

(Continued)

OTHER PUBLICATIONS

Definition of "orthopedics", Stedman's Medical Dictionary 27th Edition.*

*Primary Examiner* — Tatyana Zalukaeva
*Assistant Examiner* — Ilya Treyger
(74) *Attorney, Agent, or Firm* — Harrington & Smith

(57) ABSTRACT

A device for collecting liquid and, in particular, a device for collecting liquid or liquid-like substances used and/or generated in the course of medical procedures, the device including a bag-like product that is removable attachable to the site being treated, such as the ear or the nose, and including at least one opening for transporting the flushing liquid or other liquid-like substance from the site being treated into the bag. In accordance with the invention, the bag includes a collection section to be placed at the site being treated and a connecting support section that extends at least over the patient's one shoulder, the bag being designed to be supported on at least one shoulder when being used.

11 Claims, 3 Drawing Sheets

(56) References Cited

U.S. PATENT DOCUMENTS

| | | | | |
|---|---|---|---|---|
| 2,629,870 A | * | 2/1953 | Hudson | 2/49.1 |
| 2,782,420 A | * | 2/1957 | Barager | 2/49.3 |
| 3,001,646 A | * | 9/1961 | Cooper | 242/160.1 |
| 3,996,946 A | * | 12/1976 | Craig | 132/212 |
| 4,036,235 A | | 7/1977 | Hathaway | 128/292 |
| 4,201,212 A | | 5/1980 | Bradley | 128/275 |
| 4,569,341 A | * | 2/1986 | Morris | 128/853 |
| 5,107,859 A | | 4/1992 | Alcorn et al. | 128/853 |
| 5,395,357 A | | 3/1995 | Weigel | 604/346 |
| 5,778,889 A | * | 7/1998 | Jascomb | 128/849 |
| 5,970,979 A | * | 10/1999 | Christofel et al. | 128/849 |
| 6,032,670 A | * | 3/2000 | Miller | 128/849 |
| 6,725,864 B2 | * | 4/2004 | Ewonce et al. | 128/849 |
| 6,728,977 B1 | * | 5/2004 | Knight | 4/515 |
| D498,536 S | * | 11/2004 | Ewonce et al. | D24/189 |
| D592,742 S | * | 5/2009 | Makinson | D24/118 |
| 2002/0103451 A1 | * | 8/2002 | Ekey | 602/60 |

FOREIGN PATENT DOCUMENTS

| | | |
|---|---|---|
| FR | 2 769 829 | 4/1999 |
| FR | 2769829 A1 | 4/1999 |
| WO | WO 9945804 A1 * | 9/1999 |

* cited by examiner

DEVICE FOR COLLECTION OF FLUID

This application is a continuation of International Patent Application No. PCT/FI2006/000335 filed on Oct. 18, 2006.

The present invention relates to a device for collecting fluid and, in particular, a device for collecting fluid or fluid-like substances used and/or generated in the course of medical procedures, said device consisting of a bag-like product that is removable attachable to the site being treated and including at least one opening for transporting the flushing liquid or other liquid-like substance from the site being treated into the bag.

BACKGROUND OF THE INVENTION

In the treatment of humans, there are procedures that involve the spraying of liquid into the body or, more precisely, into bodily orifices in an attempt to remove substances that may cause infections or have other detrimental impact on health. A typical procedure of this type is the removal of ear wax or other impurities from the outer auditory canal. Ear wax excreted in the outer auditory canal may become lodged and hardened inside the canal causing hearing impairment and infections. When the ears are cleaned, a flushing liquid, such as water, is sprayed into the outer auditory canal to soften and finally wash out the material inside the auditory canal.

In other procedures, liquid or liquid-like substances are drained from the human body. Such procedures include antral puncture to open the sinus(es) or remove the liquid substances contained therein through the nostrils.

When these procedures are performed, the liquid from the ear or nose is collected using a range of equipment. For example, when ears are cleaned, the amount of water required is relative high, anything from 0.5 to 1.5 liters, making it necessary to use a fairly large collection device. Such devices include e.g. kidney bowls, which are placed under the ear or nose and into which the liquid flows during the procedure. If and when the kidney bowl is filled, it is emptied and the flushing is continued. Kidney bowls are made of paper, recycled paper, plastic or steel. Other types of collection devices are used as well. The kidney bowl or similar collection device is used by the nursing staff, or the patient himself holds the bowl under the ear or nose to make sure that he liquid or liquid-like substance is drained into the said collection device without soiling the clothes or the surroundings. If the collection device is held by the person performing the procedure, he or she can only use one hand for this purpose, which may complicate or prolong the procedure. If the patient holds the collection device, there is a risk of the device being tilted or over-turned when the patient makes a move in response to a sensation of pain or if the patient is unable to determine the correct location and position of the collection device. If another staff member is required to hold the collection device, the cost of treatment is increased. In difficult cases, and particularly when treating children in pain, the flushing water or the liquid being collected may splash over the patient even if the device were held by another person. This may happen especially if the patient (child) squirms during the procedure.

There is also equipment designed for flushing ears that incorporate a suction device for collecting the flushing liquid. When this type of equipment is used, there is some by-pass flow meaning that while the amount of liquid to be collected is relatively small, a kidney bowl or other such collection device must, nevertheless, be used.

In addition, there are known to be collection bags that are attached around the patient's head with a rubber band or similar. The problem is that such collection bags do not stay in position because the amount of liquid to be used may be large. Consequently, they have to be supported all the time and there is a risk of the bag falling off and the liquid spilling out. A specific problem is that if an on-sided bag is formed in between the wall membrane(s) of the bag, or such a bag is formed on both sides, the weight and pressure of the liquid may press the membranes together. This prevents the liquid from entering the bag in which case it will go somewhere else. Loose plastic membranes, in particular, are prone to develop obstacles to the free flow of liquid.

SUMMARY OF THE INVENTION

The purpose of the present invention is to provide a device for collecting liquid and, in particular, a device for collecting liquid or liquid-like substances used and/or generated in the course of medical procedures to overcome the drawbacks associated with existing collection devices. More specifically, the purpose is to provide a collection device that can be reliably fixed and supported in its position and that cannot dislocate during the procedure so as to allow the liquid to escape. Another purpose of the invention is to provide a device that is easy to use and affordance to manufacture.

The collection device in accordance with the invention includes a collection section to be placed at the site being treated with a connecting support section that extends at least over one of the patient's shoulders, whereby the bag being designed to be supported on at least one shoulder when being used. Such a device is simple and offers considerable advantages compared with the current practice and tools: a self-attaching collection bag that is supported on the patient leaves both hands of the person performing the procedure free while the patient is no longer required to hold the device in position. As a result, the person performing the procedure can use his or her free hand to adjust the flushing pressure or light while pulling the earlobe in such a way that the water jet can be aimed with greater accuracy and the procedure completed more quickly. In difficult cases, for example when performing the procedure on people in pain and/or children, there is no need for an assistant, which offers considerable savings in costs. The device in accordance with the invention, i.e. the bag, can be easily made large enough to eliminate the need to empty it from time to time, making the procedure quicker to perform. Additionally, the device is easy to manufacture and extremely affordable. Further advantages include ease of use and a high standard of hygiene.

In a preferred embodiment of the invention, the support section includes parts to be supported on both shoulders of the patient. As a result, the weight of the support section of the device is uniformly distributed between the two shoulders and the device can be made large in size.

In another preferred embodiment of the invention, the support section incorporates attachment elements for fastening the bag on the shoulders around the patient's neck. Then, the support section can be open on one side to make it possible to slip it in position around the neck from a side and then attach it on top of the shoulders using the attachment elements.

In another preferred embodiment of the invention, the support section constitutes a continuous structure with a central hole in the middle for the head. In this case, the device is put on by slipping the head through the centre hole, placing the device on the shoulders and securing it in position with the attachment elements.

In another preferred embodiment of the invention, at least the collection device includes filtering material or other material that is permeable to liquid. In this way, the wax plugs released from the ears, etc., are trapped by the filter and easier to examine. At the same time, this type of filtering material or other material ensures that no obstacles preventing the flow of the liquid are formed on the surface membranes of the collection section.

In another preferred embodiment of the invention, a protrusion or similar component is provided in the collection section for insertion inside the collection section. This type of protrusion or similar component keeps the surface membranes constituting the canal away from each other while allowing the liquid to flow downward.

In another preferred embodiment of the invention, at least the surface membranes of the collection section are made three-dimensionally incompatible. This is achieved by making depressions, notches, protrusions or other such forms in the membranes to ensure that they are dissimilar. As a result, the membranes are unable to cling together to form obstructions that would block the liquid flow, allowing the liquid to flow inside the collection and support sections.

In some preferred embodiments of the invention, a filtering material or said protrusions or similar components can be provided in the support section or the surface membranes of the support section can be made physically incompatible by using three-dimensional formations.

DESCRIPTION OF DRAWINGS

In the following, the invention is presented in greater detail with reference to the attached drawings where FIG. 1 provides an oblique top view of one device in accordance with the invention attached to the person being treated.

DETAILED DESCRIPTION

Figure 1:
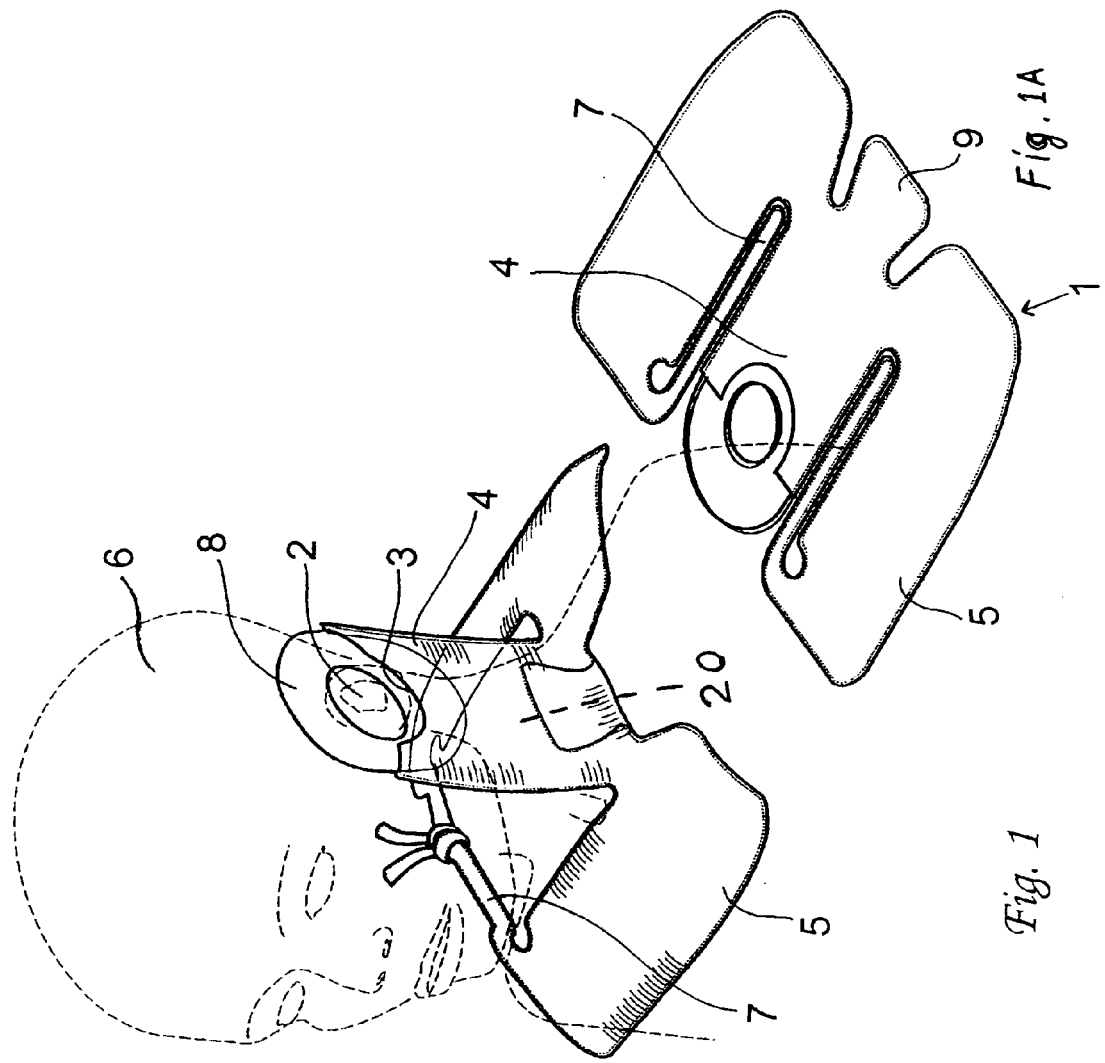
FIG. 1A is a perspective view of the device shown in FIG. 1 before attachment to the person being treated, FIG. 2 provides an oblique top view of another device in accordance with the invention attached to the person being treated.
Figure 2:
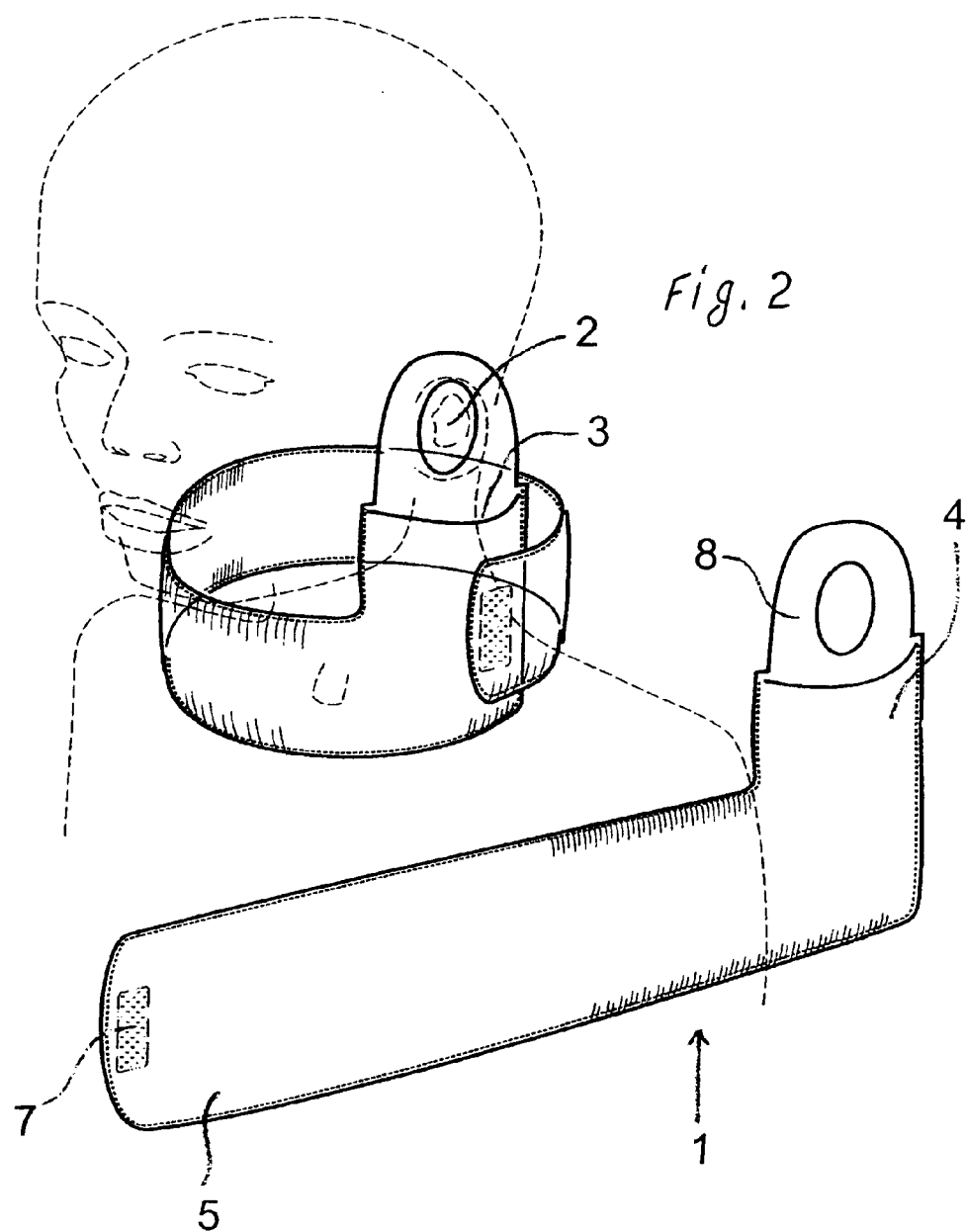
FIG. 2A is a perspective view of the device shown in FIG. 2 before attachment to the person being treated, FIG. 3 provides an oblique top view of a third device in accordance with the invention illustrated by dashed lines, said device being attached to the person being treated.
Figures 3, 3A:
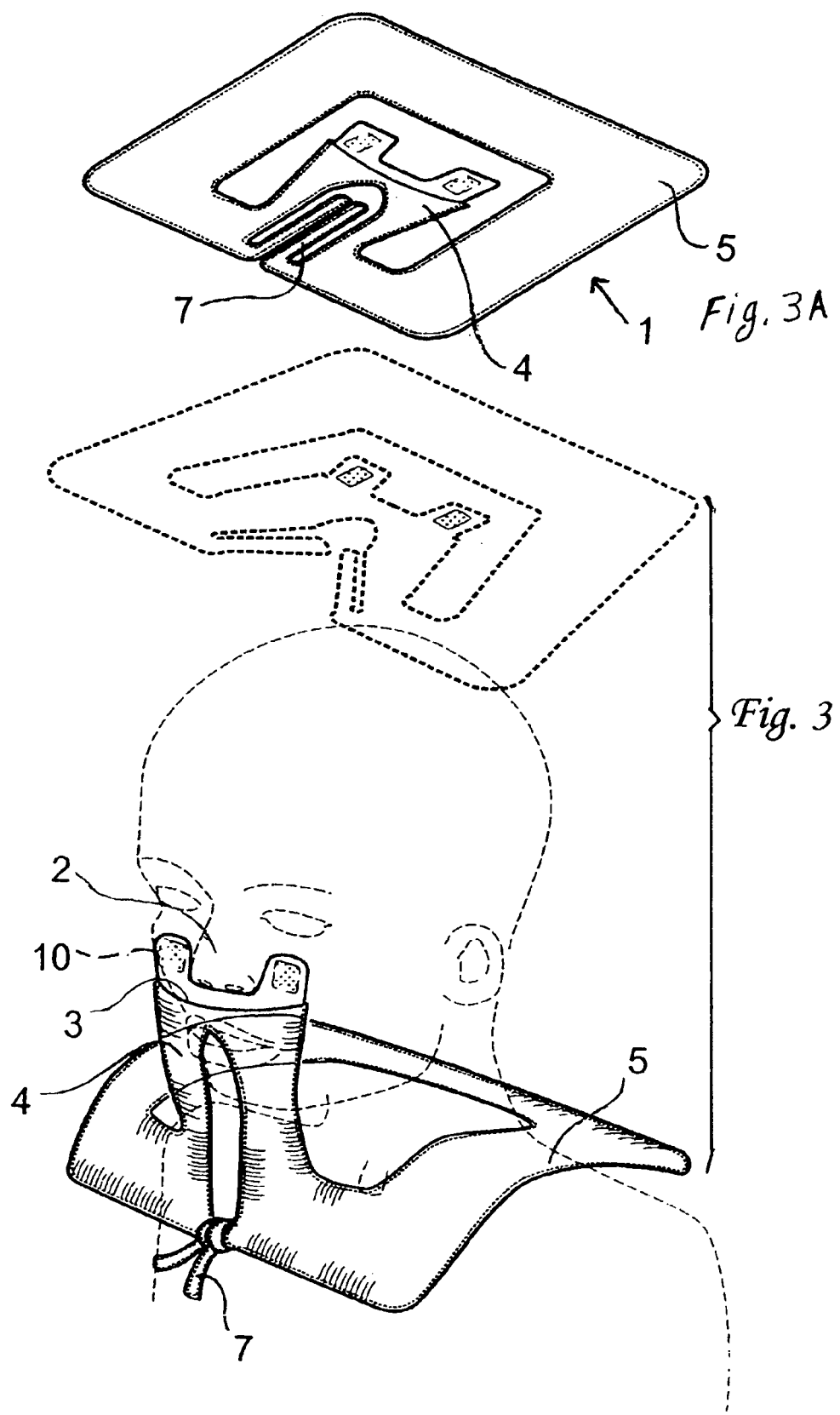
FIG. 3A is a perspective view of the device shown in FIG. 3 before attachment to the person being treated.

The devices shown in FIGS. 1 through 3 are suitable and designed for the collection of liquid and, more specifically, for the collection of liquid or liquid-like substances used and/or generated or flowing from the patient in the course of a medical procedure. The device is a bag-like product 1 that incorporates a collection section 4, with a hole 3, and a support section 5 attached to the collection section. The collection device is capable of being removable attached at the site being treated, such as the ear or nose, using appropriate means.

The embodiments shown in FIGS. 1 and 2 are intended for collecting the flushing liquid flowing out of the ear during flushing. In these embodiments, the collection section 4 includes a flap-like part 8 complete with a hole to be placed against the ear. The device can be attached to the ear either behind or under it using a suitable attachment element such as a VELCRO fastener or similar or by fitting the ear in the hole. The opening 3 of the collection section is located in the flap.

The device 1 is shown in FIG. 1 in its basic form, or packaged, with the collection section 4 in the middle and the support sections 5 on its both sides. The collection section is connected to these support sections on one side of the device. In the basic configuration, the attachment elements 7 are between the collection and support sections and fixed to the ends of supports sections. The attachment elements 7 are strip-like parts made of the same material as the rest of the bag. The attachment elements are made by cutting or otherwise forming suitable strips out of a blank. Additionally, the lower part of the collection section features a protrusion 9 that can be pushed inside the collection section to keep the gap between the surface membranes open.

When the device is used, the collection section 4 in the middle is folded up and the device is placed on both sides of the neck of the person 6 being treated, the protrusion 9 is tucked inside the collection section, the collection section is placed under the ear 2 so that the opening 3 is directly under the outer auditory canal and the strip-like attachment elements are attached to each other. As a result, the lower part of the collection section and the support sections are positioned and supported on top of the shoulder, which is on the site of the ear treated, while the attachment elements are on top of the other shoulder. When the ear is flushed, the liquid is allowed flow through the opening to the collection section and further on to the support section. The device is held firmly in position.

In the embodiment shown in FIG. 2 the device is L-shaped with an opening 3 on the top of a short side and with a flap-like part 8 in the opening. The short side constitutes the collection section 4 and the long side the support section 5. The attachment elements 7 consist of VELCRO fasteners placed at both ends of the long side. The device is placed in position by placing the collection section at the ear to be treated in such a way that the opening is right under the outer auditory canal by wrapping the support section around the neck in such a way that its lower part rests on the shoulders. The end of the support section is fixed at an appropriate location in the collection section using VELCRO fasteners.

The embodiment shown in FIG. 3 is intended for collecting liquid during antral puncture of the nose 2. In this application, the device includes a mainly circular or C-shaped support section 5, in the middle of which there is the collection section 4 when the device is its basic form packaged, while in the vicinity of the joint between the collection and support sections there are strip-like attachment elements 7 fixed to the edges of the support section. Additionally, strip-like protrusions 10 are provided on both sides of the collection opening 3 complete with VELCRO fasteners. When the device is used, it is folded out into the shape illustrated by the dashed lines, the patient's head is slipped through the mid-opening, and the middle section, i.e. the collection section, is turned up. The collection section is placed in front of the nose in such a way that the opening 3 is right under the nostrils while the strip-like protrusions and their VELCRO fasteners are on both side of the nose. Finally, the strip-like VELCRO fasteners are attached to one another and the device is ready for use. In this embodiment, the lower part of the collection section is in two parts that are connected to the support section in such a way that a breathing hole is left for the patient in between the parts of the collection section. The support sections rest and are supported on the patient's shoulders, keeping the device firmly in position during the procedure.

In some preferred embodiments of the invention, a filtering material permeable to liquid, such as illustrated by 20 in FIG. 1, can be placed in the collection section. Such filtering material may consist of cotton, foam, etc.

The devices shown in the figures are preferably made of two plastic membranes attached on top of each other by means of hot-sealing or punching. The material may consist of an appropriate plastic material, such as polyethylene (which is an affordable material). It is also possible to use a starch-based plastic material or biodegradable polylactic (lactic acid) polymer that has no impact on the carbon dioxide cycle.

The invention claimed is:

1. A device configured to collect liquid or liquid-like substances used and/or generated in the course of medical procedures, said device consisting of;
    a bag-like product that is adapted to be removably attached to a nose;
    wherein the bag-like product comprises at least one opening configured to transport the liquid or other liquid-like substances from the nose into the bag-like product;
    wherein the bag-like product includes a collection section adapted to be placed at the nose and a connecting support section which is sized and shaped to extend at least over a patient's one shoulder;
    wherein the bag-like product is sized and shaped to be supported on the at least one shoulder when being used;
    wherein the support section constitutes a continuous structure with a central hole in the middle for a head of the patient;
    wherein the support section incorporates attachment elements configured to fasten the bag-like product on both shoulders around a neck of the patient; and
    wherein a lower part of the collection section is in two parts that are connected to the support section in such a way that a breathing hole is left for the patient in between the two parts of the collection section.

2. The device in accordance with claim 1, in which at least the collection section includes filtering material permeable to liquid.

3. The device in accordance with claim 1, in which at least the collection section includes a protrusion that can be tucked inside the collection section.

4. The device in accordance with claim 1, wherein the bag-like product comprises a section proximate the opening which is sized and shaped to be located below and on opposite sides of a nose of the patient.

5. A device comprising:
    a collection section adapted to be placed at a site being treated, and
    a connecting support section which is sized and shaped to extend over at least one shoulder of a patient;
    wherein the device is adapted to be removably attached to a nose,
    wherein the device forms a bag adapted to collect liquid used and/or generated in the course of a medical procedure,
    wherein the collection section comprises at least one opening configured to transport the liquid or liquid-like substances from the nose into the device,
    wherein the support section is a continuous structure with a hole for a head of the patient to pass through,
    wherein the device is sized and shaped to be at least partially supported on the at least one shoulder when being used,
    wherein the support section comprises attachment elements configured to fasten the device around a neck of the patient, and
    wherein a lower part of the collection section is in two parts that are connected to the support section in such a way that a breathing hole is left for the patient in between the two parts of the collection section.

6. The device in accordance with claim 5, wherein the collection section includes filtering material permeable to liquid.

7. The device in accordance with claim 5, wherein the collection section includes a protrusion that can be tucked inside the collection section.

8. The device in accordance with claim 5, wherein the collection section proximate the opening is sized and shaped to be located below and on opposite sides of a nose of the patient.

9. The device in accordance with claim 8, wherein the collection section proximate the opening comprises strip-like portions adapted to be located on opposite sides of the nose.

10. The device in accordance with claim 9, wherein the support section is sized and shaped to be located on both shoulders of the patient during use, and wherein the collection section comprises a hole for the patient to breathe through.

11. The device as in claim 10, wherein the support section comprises attachment elements adapted to be connected to each other below a face of the patient.

* * * * *